(12) United States Patent
Masuda et al.

(10) Patent No.: US 10,413,645 B2
(45) Date of Patent: Sep. 17, 2019

(54) SUCTION APPARATUS FOR PERITONEAL CAVITY FLUID PERFUSION SYSTEM

(71) Applicant: NIKKISO CO., LTD., Tokyo (JP)

(72) Inventors: Yoshimichi Masuda, Higashimurayama (JP); Tatsuo Igarashi, Chiba (JP); Takuro Ishii, Chiba (JP)

(73) Assignee: NIKKISO CO., LTD., Tokyo (JP)

( * ) Notice: Subject to any disclaimer, the term of this patent is extended or adjusted under 35 U.S.C. 154(b) by 122 days.

(21) Appl. No.: 15/301,668

(22) PCT Filed: Apr. 30, 2015

(86) PCT No.: PCT/JP2015/062977
§ 371 (c)(1),
(2) Date: Oct. 3, 2016

(87) PCT Pub. No.: WO2015/170659
PCT Pub. Date: Nov. 12, 2015

(65) Prior Publication Data
US 2017/0112979 A1    Apr. 27, 2017

(30) Foreign Application Priority Data

May 8, 2014    (JP) ................................. 2014-096575

(51) Int. Cl.
*A61M 1/00* (2006.01)
*A61B 17/02* (2006.01)
(Continued)

(52) U.S. Cl.
CPC ........... *A61M 1/0064* (2013.01); *A61B 17/00* (2013.01); *A61B 17/00234* (2013.01);
(Continued)

(58) Field of Classification Search
CPC .. A61M 1/0064; A61M 1/0062; A61M 25/09; A61M 2205/3375;
(Continued)

(56) References Cited

U.S. PATENT DOCUMENTS 2,504,557 A * 4/1950 Lumian ................ A61C 17/043
433/96
2,595,666 A * 5/1952 Hutson ................ A61C 17/043
433/96
(Continued)

FOREIGN PATENT DOCUMENTS

JP    H06-189893 A    7/1994
JP    2007-279514 A    10/2000
(Continued)

OTHER PUBLICATIONS

Oct. 27, 2017 Search Report issued in European Patent Application No. 15789581.4.
(Continued)

*Primary Examiner* — Quynh-Nhu H. Vu
(74) *Attorney, Agent, or Firm* — Oliff PLC

(57) ABSTRACT

When sucking a fluid within a body cavity, foreign matter included in the fluid which exceeds the filtering diameter of a filtering apparatus may cause clogging of the filtering apparatus. Another concern is that a body cavity membrane getting stuck to a suction port of a suction tube may lead to the suction port being closed off. In response to such problems as these, provided is a suction apparatus, comprising a suction tube, and a filter member. The suction tube has side holes formed in a tube wall on a body cavity-side tail end part. The filter member has a tubular cap shape and covers a tail end aperture of the suction tube and the side (Continued)

holes, is formed from a foam body with an average aperture opening of 500-1000 μm, and has a thickness of 7.5 mm or more.

16 Claims, 6 Drawing Sheets

(51) Int. Cl.
*A61B 17/00* (2006.01)
*A61M 3/02* (2006.01)
*A61M 25/09* (2006.01)

(52) U.S. Cl.
CPC ......... *A61B 17/0218* (2013.01); *A61M 1/008* (2013.01); *A61M 1/0058* (2013.01); *A61M 1/0062* (2013.01); *A61M 3/0229* (2013.01); *A61M 1/0056* (2013.01); *A61M 25/09* (2013.01); *A61M 2205/3375* (2013.01); *A61M 2205/7563* (2013.01); *A61M 2210/1021* (2013.01)

(58) Field of Classification Search
CPC .. A61M 2205/7563; A61M 2210/1021; A61B 17/00234; A61B 17/0218
USPC .......................................................... 604/29
See application file for complete search history.

(56) References Cited

U.S. PATENT DOCUMENTS

| | | | | |
|---|---|---|---|---|
| 3,324,855 A * | 6/1967 | Heimlich | ............... | A61B 17/02 401/133 |
| 4,233,025 A * | 11/1980 | Larson | ................. | A61C 17/043 433/136 |
| 5,246,422 A | 9/1993 | Favre | | |
| 5,846,216 A * | 12/1998 | Gonzales | ............... | A61M 31/00 604/2 |
| 6,068,477 A * | 5/2000 | Mahlmann | ........... | A61C 17/043 433/136 |
| 2003/0069534 A1 | 4/2003 | Work et al. | | |
| 2005/0171467 A1* | 8/2005 | Landman | ................. | A61M 1/0084 604/35 |
| 2006/0199147 A1* | 9/2006 | Mahlmann | ........... | A61C 17/043 433/96 |
| 2010/0004588 A1* | 1/2010 | Yeh | ......................... | A61M 1/16 604/28 |
| 2013/0079702 A1* | 3/2013 | Klein | .................. | A61M 1/0064 604/22 |
| 2014/0024901 A1* | 1/2014 | Vayser | ............... | A61B 1/00135 600/249 |
| 2015/0080861 A1* | 3/2015 | Ozer | .................... | A61M 1/0084 604/540 |
| 2015/0238682 A1 | 8/2015 | Teranuma et al. | | |
| 2015/0250979 A1* | 9/2015 | Loske | .................. | A61M 1/0066 600/585 |

FOREIGN PATENT DOCUMENTS

| | | |
|---|---|---|
| JP | 3301614 B2 | 7/2002 |
| JP | 2007-519501 A | 7/2007 |
| JP | 2009-101207 A | 5/2009 |
| JP | 2011-526813 A | 10/2011 |
| JP | 2012-081191 A | 4/2012 |
| JP | 2013-135802 A | 7/2013 |
| JP | 2013-135805 A | 7/2013 |
| WO | 2013/133778 A1 | 9/2013 |
| WO | 2014/046249 A1 | 3/2014 |

OTHER PUBLICATIONS

Jun. 23, 2015 Search Report issued in International Patent Application No. PCT/JP2015/062977.

* cited by examiner

SUCTION APPARATUS FOR PERITONEAL CAVITY FLUID PERFUSION SYSTEM

TECHNICAL FIELD

The present invention relates to a suction apparatus used in a body cavity fluid perfusion system.

BACKGROUND

Conventionally, laparo-endoscopic surgery called water-filled laparo-endoscopic surgery (WaFLES) has been known. In this method, endoscopic surgery is performed while fluid such as isotonic fluid is perfused in the body cavity (for example, refer to Patent Literatures 1 and 2). Filling the body cavity with the fluid can prevent drying of organs and thus adhesion thereof. The water-filled surgery has such an advantage that organs can be moved without being damaged. In addition, this fluid effectively serves as propagation medium of ultrasonic waves, which is relatively easily damped in air.

Bleeding during an operation in the body cavity and a resected tissue fragment floating in the body cavity cloud the fluid and blur an endoscope view. According to Patent Literatures 3 to 6, the fluid in the body cavity is circulated through a filtering apparatus. Specifically, as illustrated in FIG. 4, a suction tube 110 is placed in a body cavity 100 to suck the fluid in the body cavity. The sucked fluid is filtered through a filtering apparatus 112 to remove red blood cells and tissue fragments in the fluid. The fluid after the filtering is returned into the body cavity.

CITATION LIST

Patent Literature

[PATENT LITERATURE 1] Japanese Patent Laid-Open Publication No. Hei 6-189893
[PATENT LITERATURE 2] Japanese Patent Laid-Open Publication No. 2012-81191
[PATENT LITERATURE 3] Japanese Patent No. 3301614
[PATENT LITERATURE 4] Japanese Patent Laid-Open Publication No. 2013-135802
[PATENT LITERATURE 5] Japanese Patent Laid-Open Publication No. 2013-135805
[PATENT LITERATURE 6] International Publication No. WO 2014/046249

SUMMARY

Technical Problem

When the fluid sucked through the suction tube 110 includes a foreign matter having a size that exceeds the filtering diameter (for example, the inner diameter of a hollow fiber membrane) of the filtering apparatus 112, this foreign matter leads to clogging of the filtering apparatus 112.

The body cavity includes body cavity membranes such as a peritoneum and a pleura. For example, a greater omentum 116 as a peritoneum hangs from a stomach 114 toward the intestine in the peritoneal cavity. Each of these body cavity membranes has a high degree of moving freedom and floats in the fluid filling the body cavity. As a result, the body cavity membrane becomes stuck to a suction port of the suction tube 110, which potentially leads to the closure of the suction port.

The present invention intends to solve these problems, and it is an object of the present invention to provide a suction apparatus for a body cavity fluid perfusion system, which is capable of preventing clogging of a filtering apparatus and closure of a suction port.

Solution to Problem

The present invention relates to a suction apparatus for a body cavity fluid perfusion system configured to fill a body cavity with fluid and circulate the fluid through a filtering apparatus. This suction apparatus includes a suction tube connecting the body cavity and the filtering apparatus and provided with a side hole formed in a wall of the tube in a body cavity-side tail end (distal end) part. The suction apparatus also includes a filter member having a tubular cap shape covering a tail end (distal end) aperture of the suction tube and the side hole when fitted on the body cavity-side tail end part of the suction tube, formed from a foam body with an average aperture opening not smaller than 500 μm and not larger than 1000 μm, and having a thickness not smaller than 7.5 mm.

In the above-described invention, the filter member preferably has such a thickness that a diameter of the filter member is smaller than an aperture diameter of a port member attached to an incisional wound.

In the above-described invention, the suction apparatus preferably includes a guide wire supporting the filter member.

In the above-described invention, at least part of the filter member preferably has an ellipsoid shape.

Advantageous Effects of Invention

The present invention can provide a suction apparatus for a body cavity fluid perfusion system, which can prevent clogging of a filtering apparatus and closure of a suction port.

DESCRIPTION OF EMBODIMENTS

Figure 1:
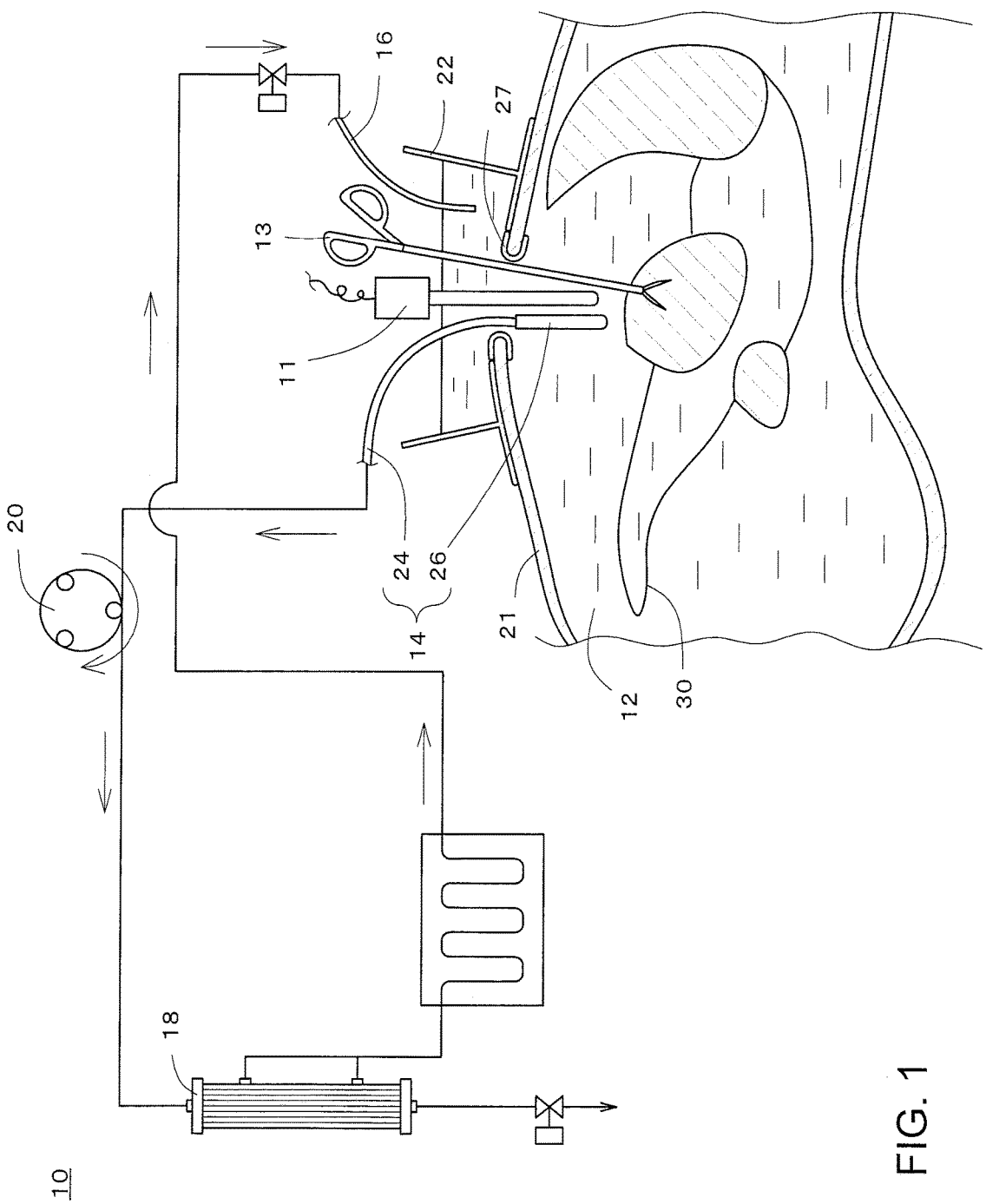
FIG. 1 is a diagram exemplarily illustrating a body cavity fluid perfusion system and a suction apparatus thereof according to the present embodiment.

FIG. 1 exemplarily illustrates a body cavity fluid perfusion system 10 according to the present embodiment. This system is used in endoscopic surgery, and is configured to fill a body cavity containing an organ as a surgery target with fluid such as isotonic fluid (isotonic sodium chloride solution) and circulate the fluid through a filtering apparatus. FIG. 1 illustrates an example in which the surgery target is an organ in the peritoneal cavity of this body cavity 12. The body cavity fluid perfusion system 10 includes a suction apparatus 14, a fluid returning tube 16, a filtering apparatus 18, a circulation pump 20, and a water tank 22.

The circulation pump 20 circulates the fluid through the body cavity 12 and the filtering apparatus 18. From a hygiene perspective, the circulation pump 20 preferably does not contact the fluid. For example, the circulation pump 20 is a roller pump.

The fluid returning tube 16 is a flow path for returning the fluid filtered by the filtering apparatus 18 to the body cavity 12. A body cavity-side tail end (distal end) of the fluid returning tube 16 may be disposed in the water tank 22.

The water tank 22 is arranged on a body wall 21 so as to surround an incisional wound of the body wall 21. The water tank 22 is provided with a through-hole in a bottom surface thereof and arranged on the body wall 21 such that the through-hole is placed over the incisional wound. The water tank 22 stores therein isotonic fluid. The stored isotonic fluid flows into the body cavity 12 through the through-hole.

The filtering apparatus 18 filters to separate, for example, a blood cell component and a tissue fragment from the fluid fed from the suction apparatus 14. The target of the separation through the filtering apparatus 18 is any material in the body cavity 12 that blurs an endoscope view. In other words, the target is any component that clouds the fluid in the body cavity 12, and specifically, is a red blood cell component or a tissue fragment of an internal organ. The filtering apparatus 18 is configured to have such a filtering diameter that these components can be separated from the fluid by filtering. For example, the filtering apparatus 18 is a hollow fiber membrane module filled with a hollow fiber membrane having an inner diameter of 200 μm.

The suction apparatus 14 includes a suction tube 24 and a filter member 26. The suction tube 24 connects the body cavity 12 and the filtering apparatus, and is driven by the circulation pump 20 to suck the fluid in the body cavity 12 and then transfer the fluid to the filtering apparatus 18. For example, the suction tube 24 is inserted, together with surgical instruments such as an endoscope 11 and a forceps 13, into the body cavity 12 through an aperture of a port member 27 attached to the incisional wound. The suction tube 24 is, for example, a circular tube. The port member 27 is, for example, a single-use retractor such as Lapprotector (registered trademark).

The suction tube 24 is preferably a narrow tube with taken into account its insertability into the port member 27 and interference with surgical instruments in the body cavity 12. For example, the suction tube 24 preferably has an outer diameter not smaller than 5.0 mm and not larger than 15.0 mm. In an example illustrated in FIG. 2, the suction tube 24 has an outer diameter PD1 of 10 mm and an inner diameter PD2 of 8 mm (with a thickness PT=1 mm). A head part of the suction tube 24 only needs to have a length large enough to connect the body cavity 12 and the filtering apparatus 18, and has, for example, a length not smaller than 200 mm and not larger than 300 mm.

The suction tube 24 may be formed from a flexible material. For example, the suction tube 24 may be a polyvinyl chloride (PVC) tube or a silicon tube. Alternatively, as illustrated in a lower part of FIG. 3, a body cavity-side tail end part 25 (distal end part) of the suction tube 24 may be formed from a rigid material, and the remaining part may be formed from the flexible material described above. Since the body cavity-side tail end part 25 is covered by the filter member 26 that is an elastic material as described later, the body cavity-side tail end part 25 does not potentially damage an organ in the body cavity 12 when formed from a rigid material such as a metal. Moreover, when formed from a rigid material, the body cavity-side tail end part 25 can withstand deformation and prevent a side hole 23 from being crushed by the deformation. Furthermore, the body cavity-side tail end part 25 formed from a metal material has such an advantage that the position of the body cavity-side tail end part 25 in the body cavity 12 can be detected using an ultrasonic sensor. The body cavity-side tail end part 25 formed from a metal material includes, for example, a metal circular tube made of stainless steel (SUS) having a thickness of 1.0 mm A lower part of FIG. 2 exemplarily illustrates a side view of the body cavity-side tail end part 25 of the suction tube 24. The side hole 23 is formed in a wall of the tube in the body cavity-side tail end part 25. The side hole 23 together with a tail end aperture 28 (distal end aperture) functions as inlets through which the fluid in the body cavity 12 is sucked, and the tube wall includes a plurality of the side holes 23. For example, the side holes 23 in a number not smaller than 100 and not larger than 200 may be formed in the body cavity-side tail end part 25. In the example illustrated in FIG. 2, 160 side holes 23 are formed in the body cavity-side tail end part 25. With this configuration, the side holes 23 function as a plurality of inlets, and closure due to sticking of a body cavity membrane 30 is unlikely to occur compared to a case in which only the tail end aperture 28 functions as an inlet.

The side holes 23 may be formed over an insertion length by which the suction tube 24 is inserted into the body cavity 12. For example, the side holes 23 are formed in a region having a length PL not smaller than 70 mm and not larger than 90 mm.

Figure 2:
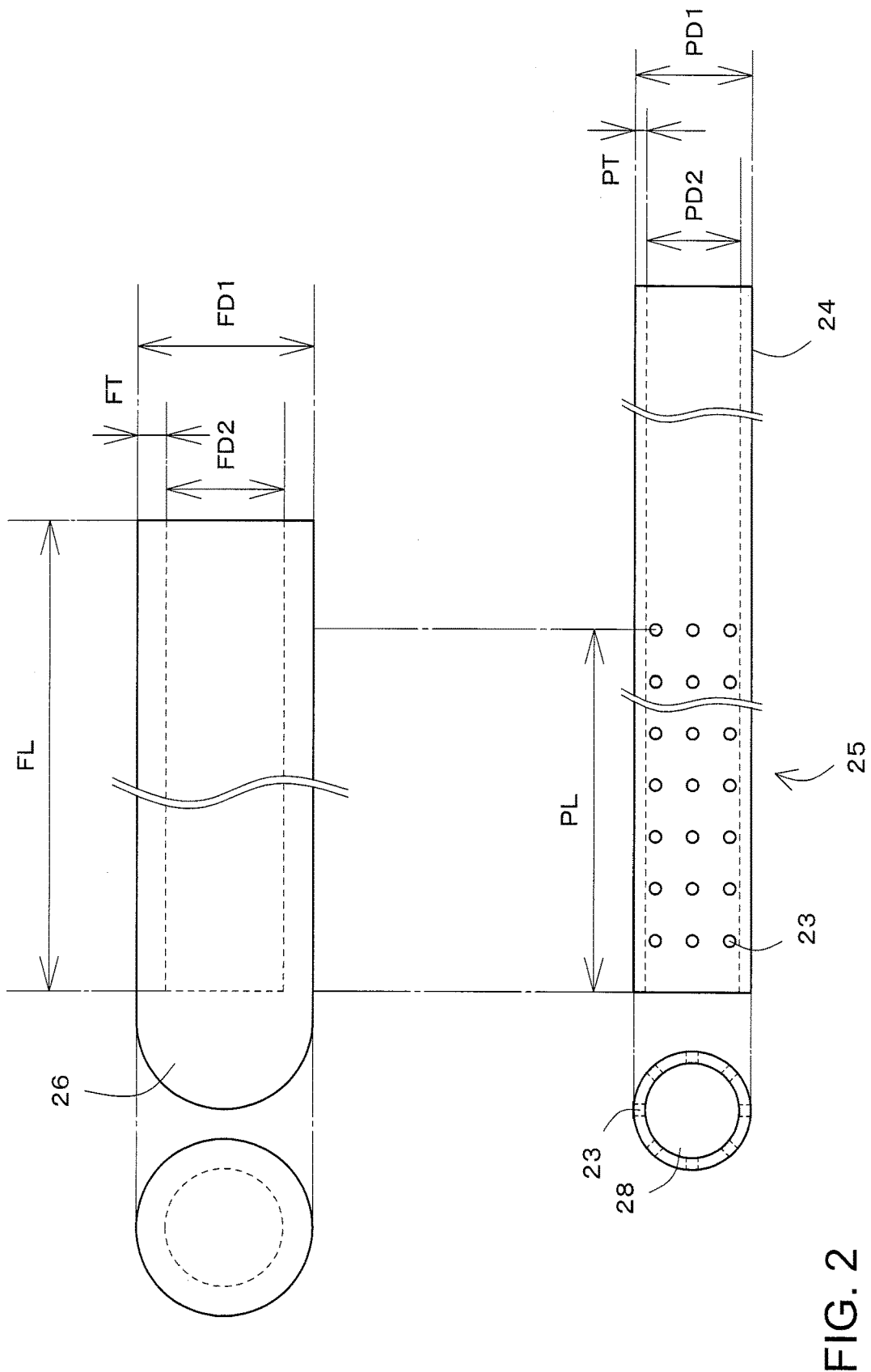
FIG. 2 is a diagram exemplarily illustrating the suction apparatus according to the present embodiment.

As illustrated in a front view of the body cavity-side tail end part 25 on a left side in the lower part of FIG. 2, the side holes 23 may be provided at an interval of 45°. As illustrated in a side view of the body cavity-side tail end part 25 on a right side in the lower part of FIG. 2, a plurality of the side holes 23 may be provided along a longitudinal direction. An interval between the side holes 23 in the longitudinal direction may be, for example, not smaller than 4.0 mm and not larger than 4.5 mm. The side holes 23 have such a diameter that a red blood cell component and a tissue fragment of an internal organ can be sucked through the side holes 23, and have a diameter of, for example, 1.0 mm.

The filter member 26 has a tubular cap shape covering the tail end aperture 28 of the suction tube 24 and the side holes 23 when fitted on the body cavity-side tail end part of the suction tube 24. The filter member 26 is formed from an elastic foam body, and has, for example, a hardness not smaller than 6.0 and not larger than 10.0. Measurement of the hardness is based on ASTM D 2240-05 "Standard Test Method for Rubber Property-Durometer Hardness", and is performed by using, for example, Type GS-754G durometer manufactured by TECLOCK Corporation.

The filter member 26 is to be inserted into the body cavity 12, and is thus formed from a material that satisfies biocompatibility. The filter member 26 is to be exposed to the fluid, and is thus preferably formed from a resin material having hydrolysis resistance. For example, the filter member 26 is formed from a continuous-cell foam body (continuous-cell foam sponge) made of an ester polyurethane material.

The filter member 26 preferably has a smooth surface shape rather than an uneven shape so as to achieve insertability into the port member 27 and prevention of damage to an organ. For example, the filter member 26 has an outer surface shape of a cylinder with a hemisphere added to a head thereof.

The filter member 26 has an inside space length sufficient to cover all side holes 23. For example, as illustrated in FIG. 2, the filter member 26 is formed to have an inside space length FL that exceeds the length PL of a side-hole formed region in the body cavity-side tail end part 25 of the suction tube 24. In the embodiment illustrated in FIG. 2, the length PL of the side-hole formed region is 80 mm, whereas the inside space length FL of the filter member 26 is 90 mm.

The thickness of the filter member 26 is set so as to prevent the closure of the suction tube 24. The body cavity membrane 30 (for example, the greater omentum) floating in the fluid that fills the body cavity 12 and stuck to the entire filter member 26 leads to the suction tube 24 being closed off. When the body cavity membrane 30 does not become entirely stuck to the filter member 26, the closure of the suction tube 24 can be avoided. Thus, the filter member 26 is formed to have a large surface area.

In addition, a suction power of the suction apparatus 14 is preferably adjusted so that the body cavity membrane 30 being in contact with the surface of the filter member 26 easily becomes separated from the filter member 26 by its buoyancy and surrounding fluid flow.

According to the above discussion, the filter member 26 preferably has a sufficient thickness. Such a thickness leads to an increased surface area in which the suction is possible. In addition, the increased surface area leads to distribution of a larger number of filters and side holes on the surface, which leads to dispersion of the suction power on a suction part. As a result, the entire suction power is reduced, thereby reducing the sticking of the body cavity membrane 30 to the filter member 26. In this manner, in the present embodiment, the thickness of the filter member 26 is appropriately determined so as to prevent the closure of the suction tube 24 by the body cavity membrane 30.

Table 1 below lists results of an experiment performed by the inventors. In this experiment, Samples 1 to 3 of the filter member 26 having various thicknesses were manufactured. Samples 1 to 3 each had the inside space length FL of 90 mm, covering all side holes 23 of the suction tube 24. Samples 1 to 3 were each formed from an open-cell (continuous-cell) sponge made of a polyester urethane foam. These samples 1 to 3 were each fitted on the suction tube 24 and inserted into the peritoneal cavity of an animal (pig). Then, isotonic sodium chloride solution was perfused into the peritoneal cavity at a flow rate of 0.5 L per minute to 3 L per minute so as to check a suction state (suction capability) of the fluid.

TABLE 1

| Sample No. | Thickness | Suction Capability |
|---|---|---|
| Sample 1 | 2.5 mm | Poor(Closed) |
| Sample 2 | 5.0 mm | Poor(Closed) |
| Sample 3 | 7.5 mm | Good(Not closed) |

According to the above experiment result, the closure of the suction tube 24 by the body cavity membrane 30 can be prevented when the filter member 26 is set to have a thickness FT not smaller than 7.5 mm The filter member 26 having too large an outer diameter makes the insertion into the body cavity 12 through the incisional wound difficult. Thus, the filter member 26 preferably has such a thickness FT that the outer diameter FD1 of the filter member 26 is smaller than the aperture diameter of the port member 27 attached to the incisional wound. Specifically, when the port member 27 has an aperture diameter of 30 mm and the suction tube 24 has the outer diameter PD1 of 10 mm, the thickness FT of the filter member 26 is preferably not larger than 10 mm.

The aperture opening (single-cell diameter) of a cell of the filter member 26 is determined taken into consideration performance in shielding of a material having a size not smaller than the filtering diameter of the filtering apparatus 18, and performance in transmission of a red blood cell component and a tissue fragment of an internal organ that otherwise lead to a degraded endoscope view.

To achieve the performance in shielding of a material having a size not smaller than the filtering diameter of the filtering apparatus 18, the average aperture opening of a cell of the filter member 26 may be set not larger than the filtering diameter of the filtering apparatus 18. However, as indicated in Table 2 to be described later, when the average aperture opening of a cell of the filter member 26 is not larger than the filtering diameter, the performance in transmission of a red blood cell component and a tissue fragment of an internal organ decreases. This is thought to be due to the thickness of the filter member 26.

As described above, the thickness FT of the filter member 26 is set to be not smaller than 7.5 mm so as to prevent the closure of the suction tube 24 due to the sticking of the body cavity membrane 30. Because of this thickness, a path made of cells is formed from the outer surface of the filter member 26 to the inside of the suction tube 24. While moving through the path, a red blood cell component and a tissue fragment of an internal organ become caught by the filter member 26, hardly reaching the suction tube 24.

Table 2 below lists experiment results on the average aperture opening of the filter member 26. In this experiment, Samples 4 to 7 having various average aperture openings were manufactured. Measurement of the average aperture opening obtained diameters was performed at 10 optional points by using a stereoscopic microscope system (product number: SZX16) manufactured by Olympus Corporation, and an average value of the diameters was also obtained.

Samples 4 to 7 each had the inside space length FL of 90 mm, covering all side holes 23 of the suction tube 24. Samples 4 to 7 each had a thickness of 7.5 mm. Samples 4 to 7 were each formed from an open-cell (continuous-cell) sponge made of a polyester urethane foam.

Spherical glass particles of 40 μm and 200 μm were put in a beaker filled with water. The former particles simulate a red blood cell component or a tissue fragment of an organ, and the latter particles simulate a material having a size that exceeds the filtering diameter of the filtering apparatus 18. Samples 4 to 7 were each fitted to the suction tube 24 and put into the beaker to check the transmission of the 40 μm particles and the shielding of the 200 μm particles.

TABLE 2

| Sample No. | Average Aperture Opening | Transmission of 40 μm Particles | Shielding of 200 μm Particles |
|---|---|---|---|
| Sample 4 | 355 μm | Small amount transmitted | Almost Total Amount shielded |
| Sample 5 | 744 μm | Total amount transmitted | Almost Total Amount shielded |
| Sample 6 | 800 μm | Total amount transmitted | Small Amount transmitted |

TABLE 2-continued

| Sample No. | Average Aperture Opening | Transmission of 40 μm Particles | Shielding of 200 μm Particles |
|---|---|---|---|
| Sample 7 | 1742 μm | Total amount transmitted | ⅓ of total amount transmitted |

As indicated by the above experiment result of Sample 4, when the average aperture opening is not larger than 355 μm, the performance in transmission of the 40 μm particles (a red blood cell component or a tissue fragment) decreases. As indicated by the experiment result of Sample 6, the performance in shielding of the 200 μm particles (material having a size that exceeds the filtering diameter) gradually decreases as the average aperture opening increases from 800 μm. According to these experiment results, the filter member 26 preferably has an average aperture opening not smaller than 500 μM and not larger than 1000 μm with the thickness being not smaller than 7.5 mm. The filter member 26 more preferably has an average aperture opening not smaller than 500 μm and not larger than 750 μm so as to improve the performance in shielding of the 200 μm particles.

Use of the filter member 26 described above allows the body cavity fluid perfusion system according to the present embodiment to prevent clogging of the filtering apparatus 18 and closure of the suction port (the side holes 23 and the tail end aperture 28) of the suction tube 24. In particular, even when a body cavity membrane such as the greater omentum becomes stuck to the suction port, the closure of the suction port can be avoided, thereby achieving an improved freedom of positioning the filter member 26 in the body cavity 12. With this improvement of the positioning freedom, a guide wire 32 may be provided so as to perform the positioning of the filter member 26 in the body cavity 12.

Figure 3:
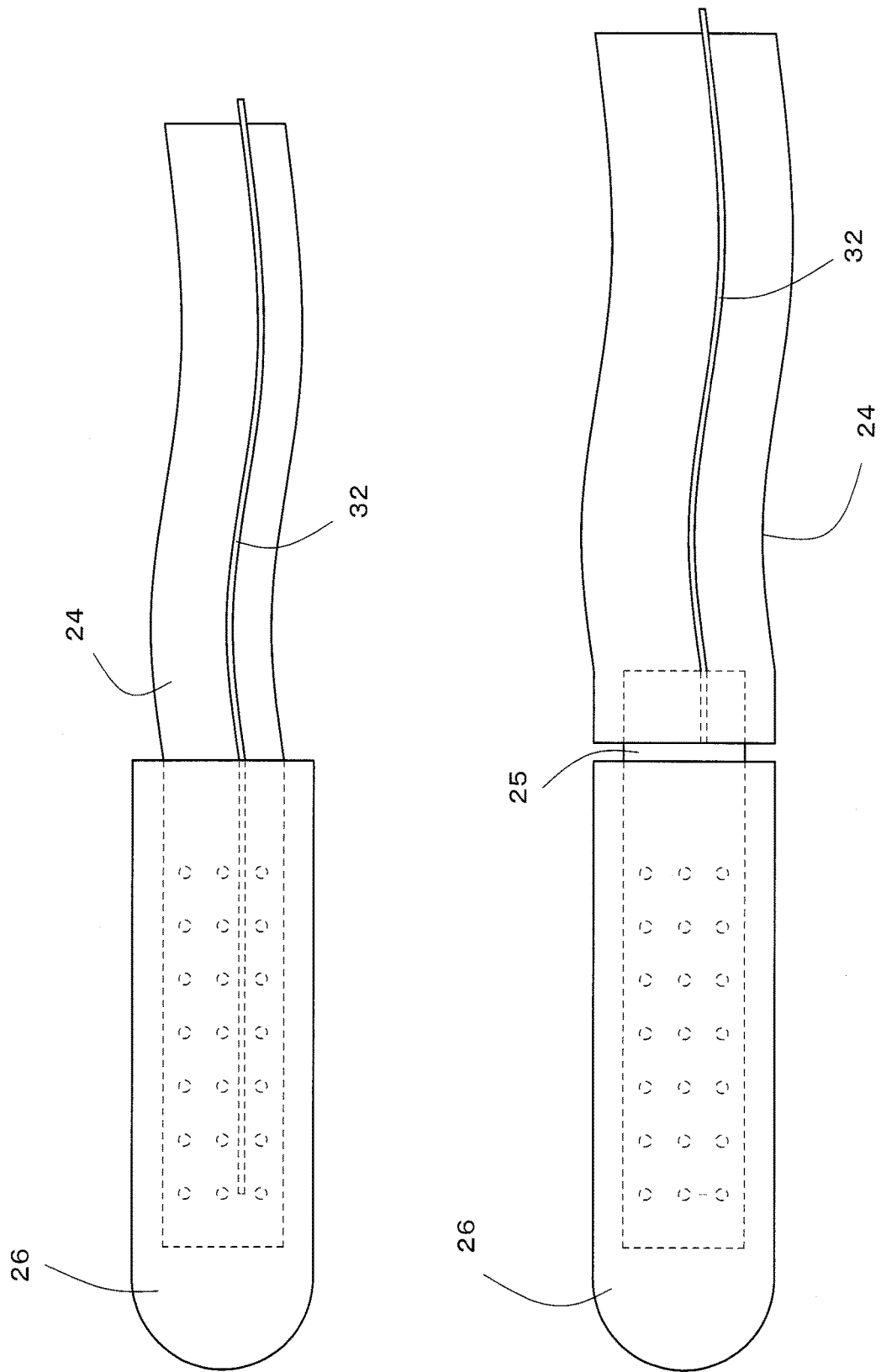
FIG. 3 is a diagram exemplarily illustrating the suction apparatus according to the present embodiment.
Figure 4:
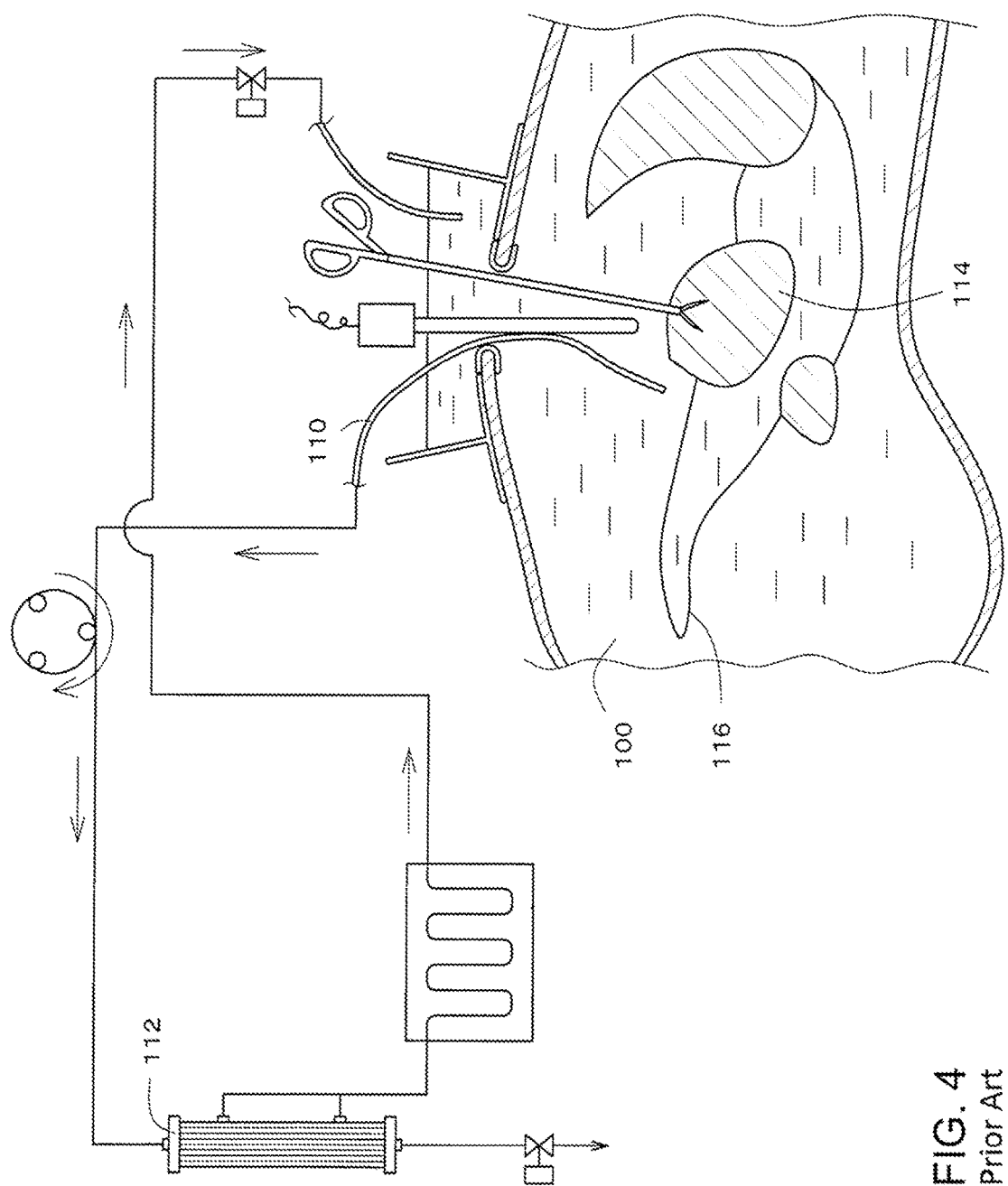
FIG. 4 is a diagram exemplarily illustrating a conventional body cavity fluid perfusion system.

FIG. 3 illustrates an example in which the guide wire 32 is attached to the suction apparatus 14. The guide wire 32 is a support member supporting the filter member 26. Specifically, the guide wire 32 has one end fixed to the filter member 26, and the other end placed outside the body cavity 12. The guide wire 32 can facilitate control of the position of the filter member 26 in the body cavity 12 from outside the body cavity 12.

The guide wire 32 may be bonded to the suction tube 24. In addition, the guide wire 32 may be used in a multiple-lumen tube so as to prevent contact with an organ in the body cavity 12.

The guide wire 32 preferably has a stiffness sufficient to withstand pressing by an organ when moved in the body cavity 12, and also has a flexibility to allow deformation in response to a force by an operator. For example, the guide wire 32 is formed from a stainless steel (SUS), a nickel-titanium alloy (NiTi), or a composite material thereof, each having a diameter of 2 mm.

<Second Embodiment>

Figure 5:
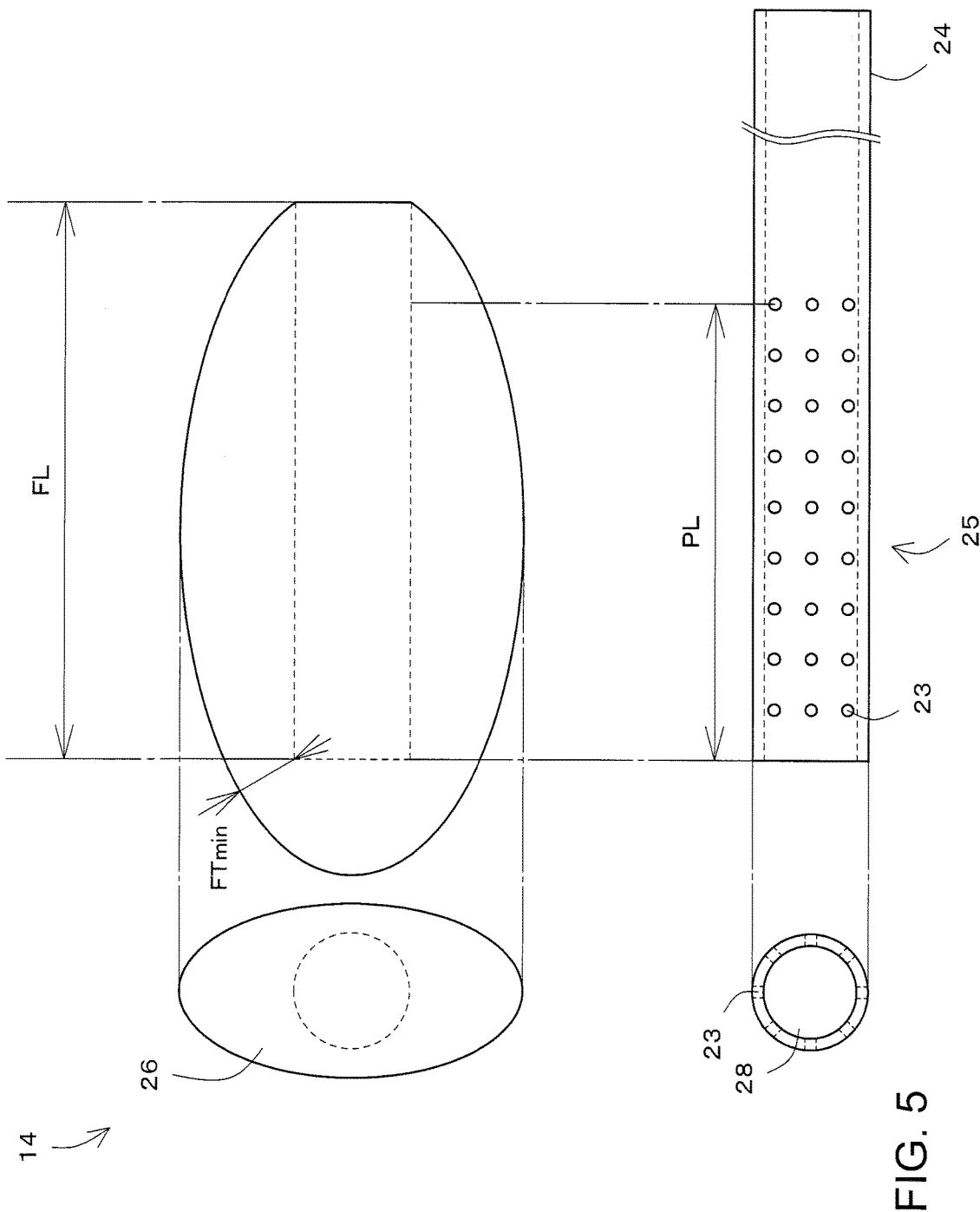
FIG. 5 is a diagram exemplarily illustrating the suction apparatus according to another example of the present embodiment.

FIG. 5 illustrates another example of the suction apparatus 14 according to the present embodiment. In this suction apparatus 14, a filter member 26' has a shape different from the shape of the filter member 26 illustrated in FIG. 2. Specifically, the filter member 26' has a flattened ellipsoid shape (gohei mochi shape). The filter member 26' on the surface of the suction tube 24 preferably has a minimum thickness FTmin not smaller than 7.5 mm when the suction tube 24 is inserted into the filter member 26'. The filter member 26' has a surface area larger than the surface area of the filter member 26.

Since the surface area of the filter member 26' is larger than the surface area of the filter member 26, a body cavity membrane, such as the greater omentum, stuck to the surface of the filter member 26' is unlikely to cover the entire surface of the filter member 26' compared to the case with the filter member 26, further reducing the possibility of closure of the suction tube 24.

<Third Embodiment>

Figure 6:
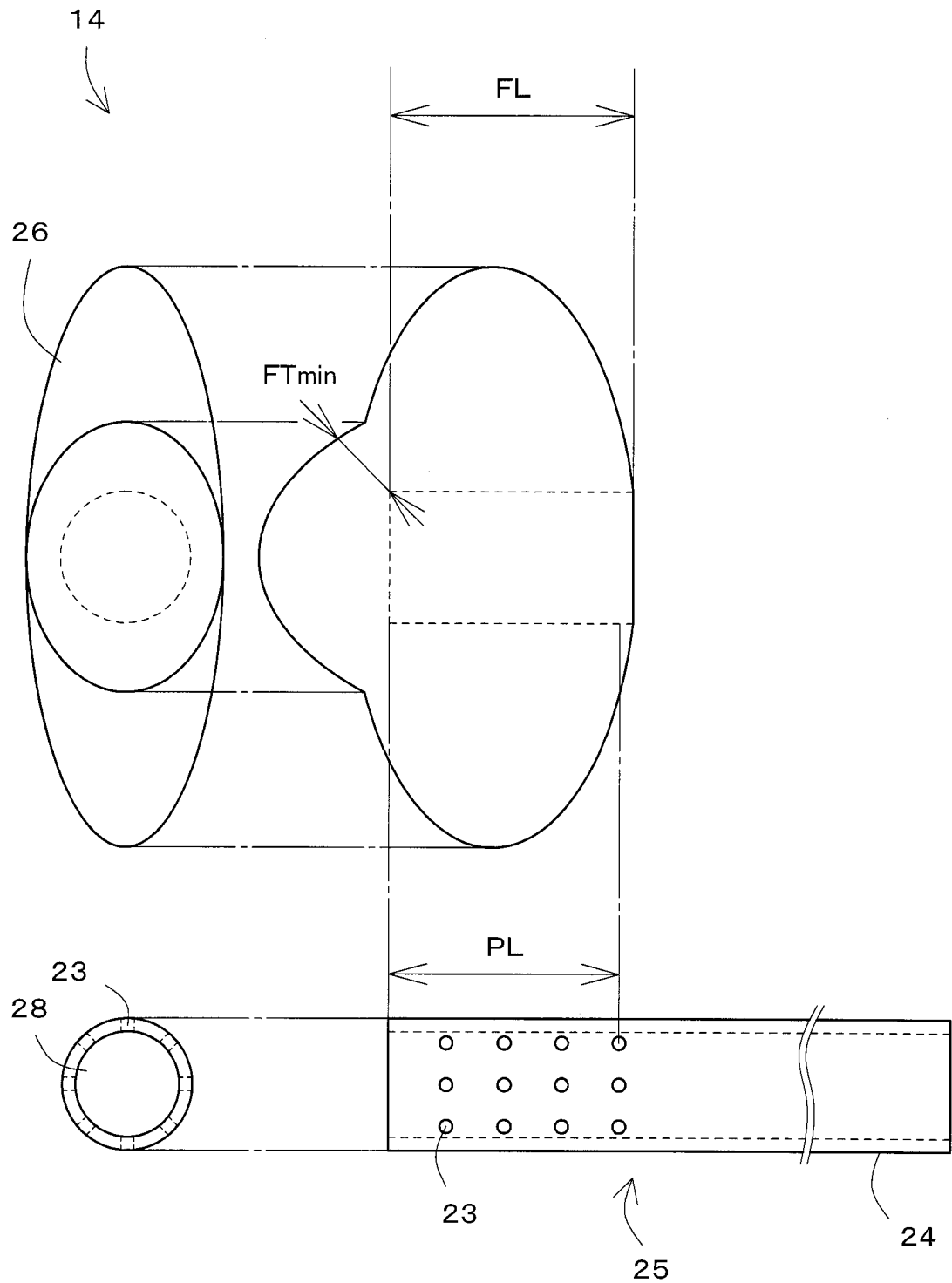
FIG. 6 is a diagram exemplarily illustrating the suction apparatus according to still another example of the present embodiment.

FIG. 6 illustrates still another example of the suction apparatus 14 according to the present embodiment. In the suction apparatus 14, a filter member 26" has a shape different from the shapes of the filter members 26 and 26' illustrated in FIGS. 2 and 5. Specifically, the filter member 26" has a three-pronged ellipsoid shape (squid fin shape). More specifically, a flattened ellipsoid has its long axis aligned with the radial direction of the inside space (and the suction tube 24), and is provided with an ellipsoid protrusion on a side opposite to a receiving aperture (insertion aperture) for the suction tube 24 in the direction of the short axis, which is orthogonal to the long axis.

The filter member 26" on the surface of the suction tube 24 preferably has a minimum thickness FTmin not smaller than 7.5 mm when the suction tube 24 is inserted into the filter member 26". The filter member 26" has a surface area larger than the surface area of the filter member 26. The inside space length FL of the filter member 26" and the length PL of the side-hole formed region in the body cavity-side tail end part 25 of the suction tube 24 inserted into the filter member 26" are smaller than the inside space length FL of the filter members 26 and 26' and the length PL of the side-hole formed region in FIGS. 2 and 5. Specifically, the inside space length FL of the filter member 26" and the length PL of the side-hole formed region in the body cavity-side tail end part 25 of the suction tube 24 inserted into the filter member 26" are not smaller than 20 mm and not larger than 50 mm Since the surface area of the filter member 26" is larger than the surface area of the filter member 26, a body cavity membrane, such as the greater omentum, stuck to the surface of the filter member 26" is unlikely to cover the entire surface compared to the case with the filter member 26, further reducing the possibility of closure of the suction tube 24.

In addition, effective drainage of perfusion fluid can be achieved by setting the inside space length FL of the filter member 26" and the length PL of the side-hole formed region of the suction tube 24 to be smaller than the inside space length FL and the length PL of the side-hole formed region in the embodiments illustrated in FIGS. 2 and 5. In other words, when medical treatment is performed while the body cavity is filled with, for example, isotonic fluid, the suction port 23 is placed at a site where suction is most needed (typically, a deepest portion in the body cavity), and a depth at which the suction is performed can be kept constant by the suction effect of the three-pronged ellipsoid shape (squid fin shape) part irrespective of the sticking of, for example, the greater omentum and a fat tissue. When the perfusion fluid is sucked from the body cavity after an operation such as endoscopic surgery, the fluid level of the perfusion fluid in the body cavity gradually decreases. When the fluid level becomes lower than the inside space length FL, the suction tube 24 sucks air and the suction of the perfusion fluid becomes difficult. When the inside space length FL and the length of the side-hole formed region are set shorter as illustrated in FIG. 6, a fluid level at which the air suction starts becomes lower than that in the embodiments illustrated in FIGS. 2 and 5, thereby effectively performing the suction of the perfusion fluid.

REFERENCE SIGNS LIST 10 body cavity fluid perfusion system
12 body cavity
14 suction apparatus
16 fluid returning tube
18 filtering apparatus
20 circulation pump
23 side hole
24 suction tube
25 body cavity-side tail end (distal end) part
26, 26', 26" filter member
27 port member
28 tail end (distal end) aperture
30 body cavity membrane
32 guide wire

The invention claimed is:

1. A suction apparatus for a peritoneal cavity fluid perfusion system, the system being configured to fill a peritoneal cavity with fluid and circulate the fluid through a filtering apparatus, the suction apparatus comprising:
   a suction tube that is configured to connect the peritoneal cavity and the filtering apparatus, the suction tube including a side hole formed in a wall of a distal end portion of the suction tube; and
   a filter member that has a tubular cap shape that covers the distal end portion of the suction tube and the side hole when fitted on the suction tube, the filter member being formed from a foam body with a plurality of cells having an average aperture opening not smaller than 500 µm and not larger than 1000 µm, and the filter member having a wall thickness not smaller than 7.5 mm,
   wherein the distal end portion of the suction tube is formed of a rigid material and a remainder of the suction tube is formed of a flexible material.

2. The suction apparatus for a peritoneal cavity fluid perfusion system according to claim 1, wherein the distal end portion of the suction tube is formed from a metal material.

3. The suction apparatus for a peritoneal cavity fluid perfusion system according to claim 1, wherein:
   the suction apparatus is configured to be used with a port member, and
   the wall thickness of the filter member is such that a diameter of the filter member is smaller than an aperture diameter of the port member.

4. The suction apparatus for a peritoneal cavity fluid perfusion system according to claim 1, further comprising a guide wire that supports the filter member, the guide wire being configured to extend along the suction tube such that a first end of the guide wire is fixed to the filter member and a second end of the guide wire is placed outside the peritoneal cavity.

5. The suction apparatus for a peritoneal cavity fluid perfusion system according to claim 1, wherein at least part of the filter member has an ellipsoid shape.

6. The suction apparatus for a peritoneal cavity fluid perfusion system according to claim 1, wherein:
   the distal end portion of the suction tube has a length that is not shorter than 70 mm and not longer than 90 mm, and
   an inside space length of the filter member is greater than the length of the distal end portion of the suction tube.

7. A suction apparatus for a peritoneal cavity fluid perfusion system, the system being configured to fill a peritoneal cavity with fluid and circulate the fluid through a filtering apparatus, the suction apparatus comprising:
   a suction tube that is configured to connect the peritoneal cavity and the filtering apparatus, the suction tube including a side hole formed in a wall of a distal end portion of the suction tube; and
   a filter member that has a tubular cap shape that covers the distal end portion of the suction tube and the side hole when fitted on the suction tube, the filter member being formed from a foam body with a plurality of cells having an average aperture opening not smaller than 500 µm and not larger than 1000 µm, and the filter member having a wall thickness not smaller than 7.5 mm.

8. The suction apparatus for a peritoneal cavity fluid perfusion system according to claim 7, wherein the suction tube has a uniform outer diameter along its length.

9. The suction apparatus for a peritoneal cavity fluid perfusion system according to claim 7, wherein the suction tube includes 100 to 200 side holes formed in the wall of the distal end portion.

10. The suction apparatus for a peritoneal cavity fluid perfusion system according to claim 7, wherein the suction tube has an outer diameter not smaller than 5.0 mm and not larger than 15.0 mm.

11. The suction apparatus for a peritoneal cavity fluid perfusion system according to claim 7, wherein the filter member has the wall thickness not larger than 10 mm.

12. The suction apparatus for a peritoneal cavity fluid perfusion system according to claim 7, wherein the distal end portion of the suction tube is formed from a metal material.

13. The suction apparatus for a peritoneal cavity fluid perfusion system according to claim 7, wherein:
   the suction apparatus is configured to be used with a port member, and
   the wall thickness of the filter member is such that a diameter of the filter member is smaller than an aperture diameter of the port member.

14. The suction apparatus for a peritoneal cavity fluid perfusion system according to claim 7, further comprising a guide wire that supports the filter member, the guide wire being configured to extend along the suction tube such that a first end of the guide wire is fixed to the filter member and a second end of the guide wire is placed outside the peritoneal cavity.

15. The suction apparatus for a peritoneal cavity fluid perfusion system according to claim 7, wherein at least part of the filter member has an ellipsoid shape.

16. The suction apparatus for a peritoneal cavity fluid perfusion system according to claim 7, wherein:
   the distal end portion of the suction tube has a length that is not shorter than 70 mm and not longer than 90 mm, and
   an inside space length of the filter member is greater than the length of the distal end portion of the suction tube.

* * * * *